(12) United States Patent
Ahn et al.

(10) Patent No.: US 9,951,361 B2
(45) Date of Patent: Apr. 24, 2018

(54) *ENSIFER* SP. STRAIN AND METHOD FOR PRODUCING PSICOSE USING SAME (71) Applicant: SAMYANG CORPORATION, Seoul (KR)

(72) Inventors: Sin Hye Ahn, Goyang (KR); Hye Jung Kim, Daejeon (KR); Eun Jin Han, Seoul (KR); Se-Hui Jeon, Daegu (KR); Chong Jin Park, Daejeon (KR); Kang Pyo Lee, Seoul (KR)

(73) Assignee: SAMYANG CORPORATION, Seoul (KR)

( * ) Notice: Subject to any disclaimer, the term of this patent is extended or adjusted under 35 U.S.C. 154(b) by 0 days.

(21) Appl. No.: 15/101,444

(22) PCT Filed: Apr. 15, 2014

(86) PCT No.: PCT/KR2014/003259
§ 371 (c)(1),
(2) Date: Jun. 3, 2016

(87) PCT Pub. No.: WO2015/099246
PCT Pub. Date: Jul. 2, 2015

(65) Prior Publication Data
US 2017/0211109 A1 Jul. 27, 2017

(30) Foreign Application Priority Data
Dec. 26, 2013 (KR) .................. 10-2013-0164686

(51) Int. Cl.
*C12P 19/24* (2006.01)
*C12P 19/02* (2006.01)
*C12N 9/90* (2006.01)

(52) U.S. Cl.
CPC ............... *C12P 19/02* (2013.01); *C12N 9/90* (2013.01); *C12P 19/24* (2013.01); *C12Y 501/03* (2013.01)

(58) Field of Classification Search
None
See application file for complete search history.

(56) References Cited

U.S. PATENT DOCUMENTS

2010/0015688 A1  1/2010  Takagi

FOREIGN PATENT DOCUMENTS

| JP | 2013-501519 | 1/2013 |
| KR | 10-2006-0125971 | 12/2006 |
| KR | 10-0832339 | 5/2008 |
| KR | 10-2011-0035805 | 4/2011 |
| KR | 10-1203856 | 11/2012 |
| WO | 2007-058086 | 5/2007 |
| WO | 2011-040708 | 4/2011 |
| WO | 2014-140633 | 9/2014 |

OTHER PUBLICATIONS

Pushpakiran G Ullapalli, et al., "Bioproduction of D-Psicose from Allitol with Enterobacter aerogenes IK7: A New Frontier in Rare Ketose Production." Biosci. Biotechnol. Biochem., 71 (12), pp. 3048-3054, Dec. 7, 2007.
Matsuo, T., Y. Baba, M. Hashiguchi, K. Takeshita, K. Izumori, and H. Suzuki., "Dietary D-psicose, a C-3 epimer of D-fructose, suppresses the activity of hepatic lipogenic enzymes in rats", Asia Pac. J. Clin. Nutr., vol. 10., Issue 3, pp. 233-237, Jan. 2001.
Matsuo, T., and K. Izumori., "D-Psicose, a rare sugar that provides no energy and additionally beneficial effects for clinical nutrition", Asia Pac. J. Clin. Nutr., vol. 13, p. S127, Jun. 2004.
Deok-Kun Oh, et al., "D-Psicose production from D-fructose using an isolated strain, *Sinorhizobium* sp.", World J Microbiol Biotechnol, vol. 23, Issue 4, pp. 559-563, Apr. 2007.
Min-Yu Chung et al., "Hypoglycemic Health Benefits of D-Psicose", Journal of Agricultural and food chemistry, vol. 60, No. 4, Feb. 1, 2012, p. 863-869.
Mu W et al, "Cloning, Expression, and Characterization of a D-Psicose 3-Epimerase from Clostridium cellulolyticum H10" Journal of Agricultural and food chemistry, vol. 59, No. 14, 2011, p. 7785-7792.
Kim Hye-Jung et al, "Characterization of an Agrobacterium tumefaciens D-Psicose 3-Epimerase That Converts D-Fructose to D-Psicose" Applied and Environmental Microbiology, Feb. 2006, vol. 72, No. 2, p. 981-985.
Zhang W et al, "Characterization of a Novel Metal-Dependent D-Psicose 3-Epimerase from Clostridium scindens 35704". PLOS One, Apr. 30, 2013, vol. 8, Issue. 4, p. 1-8.
Anne Willems et al, "Description of new Ensifer strains from nodules and proposal to transfer Ensifer adhaerens Casida 1982 to Sinorhizobium as Sinorhizobium adhaerens comb. nov. Request for an Opinion" International Journal of Systematic and Evolutionary Microbiology, 2003, vol. 53 No. 4, 1207-1217.
USPTO, Notice of Allowance of U.S. Appl. No. 15/101,459, dated May 8, 2017.
European Patent Office, European Search Report of Application No. 14875453.4, dated May 17, 2017.
European Patent Office, European Search Report of Application No. 14873792.7, dated Jul. 5, 2017.

*Primary Examiner* — Hope Robinson
(74) *Attorney, Agent, or Firm* — Lex IP Meister, PLLC (57) ABSTRACT

A novel the *Ensifer adhaerens* strain isolated from soil and a method of producing psicose using the same are provided.

7 Claims, 11 Drawing Sheets

SEQUENCE LISTING

```
<160> NUMBER OF SEQ ID NOS: 1

<210> SEQ ID NO 1
<211> LENGTH: 1334
<212> TYPE: DNA
<213> ORGANISM: Artificial Sequence
<220> FEATURE:
<223> OTHER INFORMATION: 16S rRNA of KCCM11405P

<400> SEQUENCE: 1
tgcaagtcga gcgccccgca aggggagcgg cagacgggtg agtaacgcgt gggaatctac      60 cctttctac ggaataacgc agggaaactt gtgctaatac cgtatacgcc cttcggggga     120
aagatttatc gggaaaggat gagcccgcgt tggattagct agttggtggg gtaaaggcct    180
```

-continued

```
accaaggcga cgatccatag ctggtctgag aggatgatca gccacattgg gactgagaca    240
cggcccaaac tcctacggga ggcagcagtg gggaatattg gacaatgggc gcaagcctga    300
tccagccatg ccgcgtgagt gatgaaggcc ctagggttgt aaagctcttt caccggtgaa    360
gataatgacg gtaaccggag aagaagcccc ggctaacttc gtgccagcag ccgcggtaat    420 acgaagggg ctagcgttgt tcggaattac tgggcgtaaa gcgcacgtag gcggacattt     480
aagtcagggg tgaaatcccg gggctcaacc ccggaactgc ctttgatact gggtgtctag    540
agtatggaag aggtgagtgg aattccgagt gtagaggtga aattcgtaga tattcggagg    600
aacaccagtg gcgaaggcgg ctcactggtc cattactgac gctgaggtgc gaaagcgtgg    660
ggagcaaaca ggattagata ccctggtagt ccacgccgta aacgatgaat gttagccgtc    720
gggcagttta ctgttcggtg gcgcagctaa cgcattaaac attccgcctg gggagtacgg    780
tcgcaagatt aaaactcaaa ggaattgacg ggggcccgca caagcggtgg agcatgtggt    840
ttaattcgaa gcaacgcgca gaaccttacc agcccttgac atcccgatcg cggattacgg    900
agacgttttc cttcagttcg gctggatcgg agacaggtgc tgcatggctg tcgtcagctc    960
gtgtcgtgag atgttgggtt aagtcccgca acgagcgcaa ccctcgccct tagttgccag   1020
catttagttg ggcactctaa ggggactgcc ggtgataagc cgagaggaag gtggggatga   1080
cgtcaagtcc tcatggccct tacgggctgg gctacacacg tgctacaatg gtggtgacag   1140
tgggcagcga gaccgcgagg tcgagctaat ctccaaaagc catctcagtt cggattgcac   1200
tctgcaactc gagtgcatga agttggaatc gctagtaatc gcagatcagc atgctgcggt   1260
gaatacgttc ccgggccttg tacacaccgc ccgtcacacc atgggagttg gttctacccg   1320
aaggtagtgc gcta                                                     1334
```

ENSIFER SP. STRAIN AND METHOD FOR PRODUCING PSICOSE USING SAME

TECHNICAL FIELD

The present disclosure relates to a novel the *Ensifer adhaerens* strain isolated from soil and a method of psicose using the same.

BACKGROUND ART

Psicose is a C-3 epimer of D-fructose which is 70% as sweet as D-fructose, and thus finds application as a sugar ingredient of various functional foods for use in blood sugar control, dental cavity prevention, and hepatic lipogenesis inhibition.

Sugar alcohols, widely used as alternatives to sugar, have the side effect of causing diarrhea upon uptake of a certain amount or more whereas no side effects are known for psicose. Hence, psicose has attracted intensive interest to the use thereof as a sweetener, but since psicose is rarely found in nature, its effective production is a premise for application to the food industry.

Conventionally, psicose is chemically produced from D-fructose through the catalysis of molybdic acid ions. In the meantime, a biological method using a psicose epimerase from *Agrobacterium tumefaciens* has recently been known as one of the most efficient approaches. The chemical method suffers from the disadvantage of producing only a very small amount of psicose during molasses treatment or glucose isomerization, the process is expensive, and it generates by-products. Also, the biological method is disadvantageous in that the production is of high cost and is low in yield.

Therefore, there is a need for a method by which psicose can be produced at a temperature and pH condition suited for industrialization, with high yields and no by-product generation.

DISCLOSURE

Technical Problem

An embodiment provides a method of isolating a strain with an activity of producing psicose from fructose from soil.

Another embodiment provides an *Ensifer* sp. strain with an activity of producing psicose.

Still another embodiment provides a composition for producing psicose, comprising at least one selected from the group consisting of cell, cell culture and cell lysate of *Ensifer* sp.

Yet another embodiment provides a method of producing psicose, using at least one selected from the group consisting of at least one selected from the group consisting of cell, cell culture and cell lysate of *Ensifer* sp strain.

Technical Solution

A novel *Ensifer adhaerens* strain having high activity of converting D-fructose to psicose is isolated and identified, the conversion rate of psicose from fructose is analyzed by using the strain, and the reaction conditions of pH, temperature, and the dependency of metal ion are examined for establishing the production condition optimized for mass production, and then the present inventors completes the present invention.

Another embodiment provides an *Ensifer* sp. strain with an activity of producing psicose and the *Ensifer* sp. strain is *Ensifer adhaerens*.

In another embodiment, a method of producing psicose is provided by using the strain. In the method, the cell reaction conditions optimized for high conversion rate of psicose and the conditions for mass production of psicose are provided.

The present invention will be explained in more detail.

Novel *Ensifer* sp. strain is provided. The *Ensifer* sp. strain has a high activity of converting fructose to psicose, and is at least one selected from the group consisting of *Ensifer adhaerens*, *Ensifer garamanticus*, *Ensifer sojae*, *Ensifer mexicanus*, *Ensifer numidicus*, and the like, for example *Ensifer adhaerens*.

The *Ensifer* sp. strain is *Ensifer adhaerens* SYG29 deposited as an Accession No of KCCM11405P. *Ensifer adhaerens* has 16s rRNA having an nucleotide sequence of SEQ ID NO:1, has activities of nitrate reduction, urease, beta-glucosidase, and beta-galactosidase and can metabolize the substrates of D-glucose, L-arabinose, D-mannose, D-mannitol, N-acetyl glucosamine, D-maltose and Malic acid. In addition, the *Ensifer* sp. strain has no activities of L-tryptophan degradation, D-glucose fermentation, Arginine dihydrolase, gelatin hydrolysis, utilization of Potassium gluconate, Capric acid utilization, Adipic acid utilization, Trisodium citrate utilization, and Phenylacetic acid utilization.

The *Ensifer* sp. strain has a high activity of converting fructose to psicose. The psicose conversion capability is due to an enzyme of converting fructose to psicose of the stain. The *Ensifer* sp. strain can produce an enzyme having a high activity of converting fructose to psicose, or the enzyme in a large amount, thereby providing the excellent psicose productivity. The *Ensifer* sp. strain can be used for psicose production and increase the production yield.

Accordingly, a composition for producing psicose including at least one selected from the group consisting of a cell of *Ensifer* sp. strain, cell culture and cell lysate is provided. The cell culture includes an enzyme produced by *Ensifer* sp. strain, and may contain the cell of *Ensifer* sp. strain or is cell-free solution. The cell lysate means cell lysate of *Ensifer* sp. strain or the supernatant obtained by centrifuging the cell lysate, and thus includes an enzyme produced by *Ensifer* sp. strain. Unless stated otherwise herein, the *Ensifer* sp. strain or *Ensifer* sp cell means at least one selected from the group consisting of a cell mass of the strain, a culture of the strain and a lysate of the strain.

In another embodiment, a method of producing psicose by using *Ensifer* sp. strain is provided. The method comprises a step of reacting *Ensifer* sp. with fructose. In an embodiment, the step of reacting *Ensifer* sp. with fructose is performed by culturing *Ensifer* sp. on the culture medium including fructose. In another embodiment, the step of reacting *Ensifer* sp. with fructose includes for examples, a step of mixing fructose with *Ensifer* sp. strain (for examples, at least one selected from the group consisting of cell, cell culture, and cell lysate of *Ensifer* sp.), or a step of contacting the fructose with a support immobilized with *Ensifer* sp. strain. The reaction of *Ensifer* sp. strain with fructose can convert fructose to psicose, so as to obtain psicose from fructose.

For effective production of psicose in the method, D-fructose, serving as a substrate, is used at a concentration of 40 to 75% (w/v) in the reaction mixture, for example, at a concentration of 50 to 75% (w/v). The concentration lower than the lower limit of D-fructose concentration may decrease the economic feasibility of psicose in this manner.

On the other hand, if present at a concentration higher than the upper limit, D-fructose is less apt to dissolve. Hence, the concentration preferably falls within the range. D-fructose may be in the form of a solution in a buffer or water (e.g., distilled water).

The reaction may be carried out at a pH of 6 to 9.5, for example, at a pH of 7 to 9, at a pH of 7 to 8, or at a pH of 8 to 9. In addition, the reaction may be conducted at a temperature of 30° C. or higher, for example, at a temperature of 40° C. or higher. However, the substrate D-fructose may be apt to undergo browning at 80° C. or higher. Hence, the reaction may be conducted under the temperature condition of from 40 to 80° C., for example, from 50 to 75° C., from 60 to 75° C., or from 68 to 75° C. In addition, a longer period of reaction time leads to a higher conversion rate of psicose. It is recommended to conduct the reaction for 1 hr or longer, for example, 2 hours or longer, 3 hours or longer, 4 hours or longer, 5 hours or longer, or 6 hrs or longer. However, the reaction time is preferably set forth within 48 hours since when the reaction time is extended over 48 hours, the increment of the conversion rate of psicose becomes slight, or may be decreased. Hence, the reaction time may be set forth to range from 1 to 48 hours, from 2 to 48 hours, from 3 to 48 hours, from 4 to 48 hours, from 5 to 48 hours, or from 6 to 48 hours. In consideration of industrial and economic aspects, the reaction time may fall within the range of 1 to 48 hours, 2 to 36 hours, 3 to 24 hours, 3 to 12 hours, or 3 to 6 hours, but is not be limited thereto. This condition is selected in order to maximize the conversion yield from D-fructose to psicose.

In addition, in the psicose-producing method, its concentration may be set forth to range from 5 mg(dcw: dry cell weight)/ml or higher in the entire reaction mixture, for example, range from 5 to 100 mg(dcw)/ml, from 10 to 90 mg(dcw)/ml, from 20 to 80 mg(dcw)/ml, from 30 to 70 mg(dcw)/ml, from 40 to 60 mg(dcw)/ml, or from 45 to 55 mg(dcw)/ml. If the concentration of cell mass is below the lower limit, poor or almost no conversion activity of psicose is exhibited. On the other hand, a concentration exceeding the upper limit means crowding of cells which are likely to act as an obstructer to the optimization of the entire conversion yield of psicose.

The activity of enzyme (for example, epimerase) to convert fructose to psicose may be controlled by metal ions. Hence, the presence of a metal ion may promote the reaction catalyzed by the enzymatic protein, thus increasing the production yield of psicose. The method of producing psicose by using *Ensifer* sp. strain includes a step of adding the metal ion. In an embodiment, the metal ion can be added to the culture medium during the cell culture or the culture can be performed on the culture medium added by the metal ion. In another embodiment, the metal ion can be added to the substrate including fructose, or a mixture of fructose and *Ensifer* sp. strain. In further embodiment, the metal ion can be added to the support immobilized by *Ensifer* sp. strain, a mixture of fructose and the support immobilized by *Ensifer* sp. strain, or a mixture with fructose.

The metal ion may be selected from the group consisting of a copper ion, a manganese ion, a calcium ion, a magnesium ion, a zinc ion, a nickel ion, a cobalt ion, an iron ion, and an aluminum ion and any combination thereof. For example, the metal ion can be a manganese ion, magnesium ion, a nickel ion, a cobalt ion or a mixture thereof, or can be a manganese ion, a cobalt ion or a mixture thereof. When the amount of the metal ion is below 0.5 mM, there is only a slight effect on an improvement in the production yield of psicose. Thus, the metal ion is used in an amount of 0.5 mM or greater. On the other hand, when the amount of the metal ion exceeds 5 mM, the effect of addition is insignificant compared to the surplus amount. The amount of the metal ion is set forth to be 5 mM or less. For example, the metal ion is used in an amount of 0.5 to 5 mM, for example 0.5 to 2 mM.

So long as it establishes an environment for maintaining the activity of the strain or the enzymatic protein produced from the strain for a long period of time, any support configured to immobilize the strain or the enzymatic protein thereto may be used. For example, sodium alginate may serve as the support. Sodium alginate, a naturally occurring colloidal polysaccharide abundantly found in the cell walls of brown algae, consists of β-D-mannuronic acid and α-L-gluronic acid, with a covalent β1-4 linkage therebetween. Allowing for the stable immobilization of the strain or the enzyme thereto, the linear polymer may be advantageous for the production yield of psicose. In one embodiment, a 1.5~4.0% (w/v) sodium alginate solution (e.g., aqueous sodium alginate solution), for example, an about 2.5% (w/v) sodium alginate solution may be used for immobilizing the strain. By way of example, a cell mass of the strain, a culture broth containing the enzyme produced by the strain, or a lysate of the strain is mixed with 1 to 2 volumes of an aqueous sodium alginate solution, and the mixture is dripped to a 0.2 M calcium ion solution using a syringe pump and a vacuum pump, to form beads to which the cell mass of the strain, the culture containing the enzyme produced by the strain, or the lysate of the strain are immobilized. The enzyme may be purified from the strain, a culture of the strain or a lysate of the strain using a typical method, for instance, dialysis, precipitation, adsorption, electrophoresis, affinity chromatography, or ion exchange chromatography.

In the production of psicose, a non-ionic surfactant can be used additionally to increase the psicose productivity. The non-ionic surfactant increases the permeability to cell membrane and makes the enzyme inside the cell release, thereby improving the psicose productivity. The non-ionic surfactant may be octylphenol ethoxylate (TRITON X-100®; $C_{14}H_{22}O(C_2H_4O)n$; n=9 or 10)(see FIG. 11).

The composition for producing psicose including *Ensifer* sp. strain includes further the non-ionic surfactant, such as octylphenolethoxylate. The method of producing psicose includes further a step of adding the non-ionic surfactant. In an embodiment, the non-ionic surfactant can be added to culture medium during the cell culturing stage, or the cell culture can be performed on the culture medium added by the non-ionic surfactant. In another embodiment, the non-ionic surfactant can be added to a reacting substrate including fructose, or a mixture of reacting substrate and *Ensifer* sp. strain. In further embodiment, the non-ionic surfactant can be added to the support immobilized by *Ensifer* sp. strain, a mixture of fructose and the support immobilized by *Ensifer* sp. strain, or a mixture with fructose.

The amount of added non-ionic surfactant can be determined by considering the psicose production yield, and can be 0.01 to 0.5% (v/v), for examples 0.05 to 0.45% (v/v), 0.2 to 0.45% (v/v), or 0.3 to 0.42% (v/v).

Figure 11:
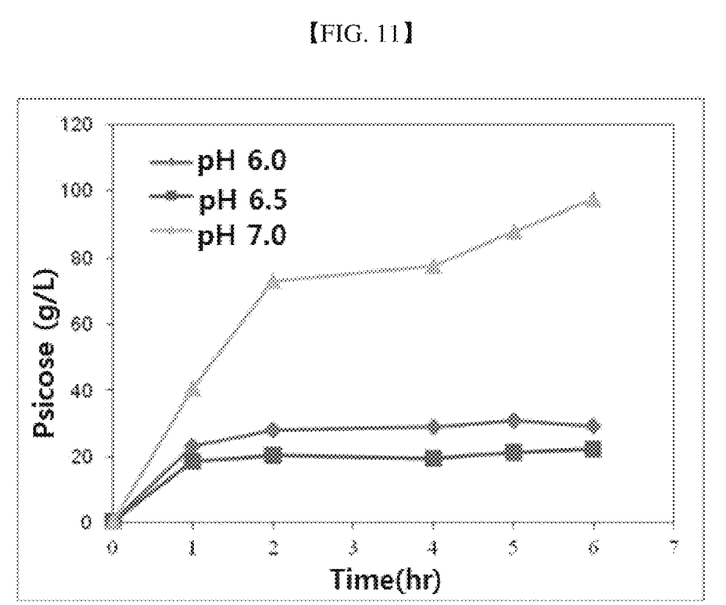
FIG. 11 is a graph showing the psicose productivity on the initial pH condition of the reaction substrate which is controlled by using HCL and NaOH, without using a buffer solution.

The method of producing psciose in accordance with the present invention uses cell to convert fructose to psicose without using a buffer solution, thereby producing psicose at a high yield using a simple process. As shown in FIG. 11, when the reaction is performed at a pH ranges (for examples, pH 7-9, pH 7-8 or pH 8-9) without using a buffer solution, the conversion rate of psicose is maintained at a high level, compared to the reaction performed at outside of pH range.

After being produced from D-fructose using the method of the present invention, psicose can be purified by a typical method which can be readily selected by a person skilled in the art, for example, from the group consisting of centrifugation, filtration, crystallization, ion exchange chromatography, and a combination.

Advantageous Effects

The novel *Ensifer* sp. strain of the present invention has the activity of producing psicose, and is superior in thermal stability under an industrially applicable condition, and thus can be expected to find useful wide applications in various functional food and pharmaceutical.

MODE FOR INVENTION

A better understanding of the present invention may be obtained through the following examples which are set forth to illustrate, but are not to be construed as the limit of the present invention.

Example 1: Isolation of the Soil Bacterium with Activity of Converting D-Fructose to Psicose The minimal medium ($KH_2PO_4$ 2.4 g/L, $K_2HPO_4$ 5.6 g/L, $(NH_4)_2SO_4$ 2.6 g/L, $MgSO_4\cdot7H_2O$ 0.1 g/L, yeast extract 1 g/L) containing 1 psicose was used.

In 10 mL of 0.85% (w/v) NaCl was suspended 1 g of rhizosphere soil, and 100 ul (microliters) drawn from the suspension was spread over an agar plate and incubated at 30° C. Among the colonies formed on the agar plates, selection was made of those distinct in shape and size. The selected colonies were inoculated into a minimal medium, and cultured at 30° C. for 24 hours with agitation. Centrifugation recovered a cell mass. This cell mass was suspended in 100 μL of a 50 mM PIPES (piperazine-N,N'-bis(2-ethanesulfonic acid)) buffer (pH 8.0) and lyzed using an ultrasonic processor (ColepParmer). After centrifugation of the lysate at 12,000 rpm and 4° C. for 10 mM, the supernatant thus formed was recovered and used as a crude enzyme. 10 mM Psicose was treated as a substrate at 30° C. for 8 hours with the crude enzyme.

Conversion from psicose to D-fructose was monitored by thin layer chromatography (TLC) and high-performance liquid chromatography (HPLC). TLC analysis was performed using a 20 cm×5 cm silica gel (Silica gel 60 F254 (Merck, Germany)) solid phase, with development with a mixture of 85:15 acetonitrile and water as a mobile phase for 3.5 min twice. For HPLC, Refractive Index Detector (Agilent 1260 RID) equipped with Aminex HPX-87C column (BIO-RAD) was used. Water served as a mobile solvent at a flow rate of 0.6 ml/min at 80° C.

Figure 1:
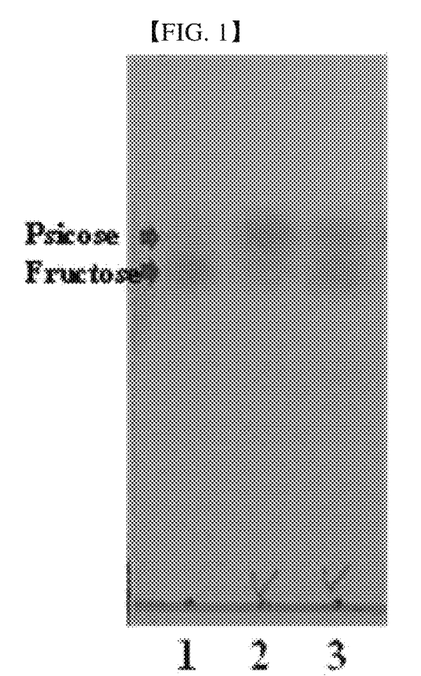
FIG. 1 is a photograph of TLC analysis showing the fructose production from psicose by using isolated *Ensifer* sp. strain in accordance with an embodiment of present invention (1: standard of fructose or psicose, 2 to 3: the fructose produced by using a supernatant obtained from the cell lysate of isolated *Ensifer* sp. strain).

The result of TLC analysis was shown in FIG. 1

Figure 2:
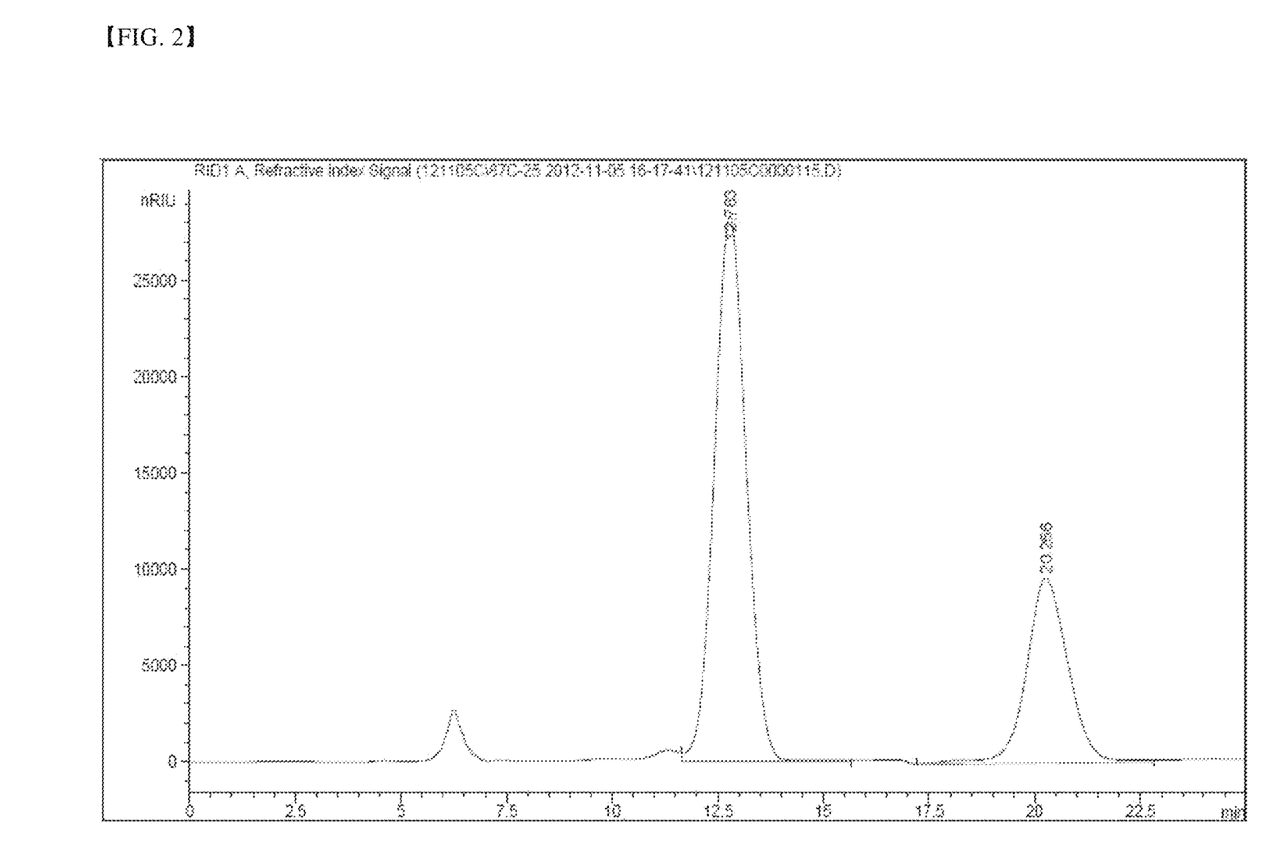
FIG. 2 is a HPLC chramatograph showing the psicose production from a high concentration of fructose.

According to the TLC analysis result, the stain having an activity of converting psicose to fructose was selected, and then were inoculated into a minimal medium containing 1% (w/v) fructose and 0.05% (w/v) psicose, and cultured at 30° C. for 24 hours. Cell mass was recovered by centrifugation. The cell mass was washed with 0.85% (w/v) NaCl, and suspended at a concentration of 40 mg-dcw/ml in 50 mM PIPES buffer (pH 8.0) containing 400 g/L fructose and 1 mM manganese ions, and reacted with D-fructose at 70° C. for 6 hours, followed by terminating the reaction by heating the reaction mixture at 100° C. for 5 min. HPLC analysis confirmed the production of psicose. For HPLC, Refractive Index Detector (Agilent 1260 RID) equipped with Aminex HPX-87C column (BIO-RAD) was used under the condition described above (solvent: water; temperature: 80° C.; flow rate: 0.6 ml/min). The results are given in FIG. 2. Final selection was made of one strain which was found to produce psicose in the greatest amount, as analyzed by HPLC analysis in FIG. 2.

Example 2: Identification of Bacterium with Activity of Converting D-Fructose to Psicose In order to identify the stain isolated in Example 1, the nucleotide sequence of 16s rRNA and the biochemical properties were analyzed. The nucleotide sequence of 16s rRNA is shown in SEQ ID NO:1 as indicated below.

```
<Nucleotide sequence of 16s rRNA>
5' -> TGCAAGTCGAGCGCCCCGCAAGGGGAGCGGCAGACGGGTGAGT

AACGCGTGGGAATCTACCCTTTTCTACGGAATAACGCAGGGAAACTTGT

GCTAATACCGTATACGCCCTTCGGGGGAAAGATTTATCGGGAAAGGATG

AGCCCGCGTTGGATTAGCTAGTTGGTGGGGTAAAGGCCTACCAAGGCGA

CGATCCATAGCTGGTCTGAGAGGATGATCAGCCACATTGGGACTGAGAC

ACGGCCCAAACTCCTACGGGAGGCAGCAGTGGGGAATATTGGACAATGG

GCGCAAGCCTGATCCAGCCATGCCGCGTGAGTGATGAAGGCCCTAGGGT

TGTAAAGCTCTTTCACCGGTGAAGATAATGACGGTAACCGGAGAAGAAG

CCCCGGCTAACTTCGTGCCAGCAGCCGCGGTAATACGAAGGGGGCTAGC

GTTGTTCGGAATTACTGGGCGTAAAGCGCACGTAGGCGGACATTTAAGT
```

-continued
CAGGGGTGAAATCCCGGGGCTCAACCCCGGAACTGCCTTTGATACTGGG

TGTCTAGAGTATGGAAGAGGTGAGTGGAATTCCGAGTGTAGAGGTGAAA

TTCGTAGATATTCGGAGGAACACCAGTGGCGAAGGCGGCTCACTGGTCC

ATTACTGACGCTGAGGTGCGAAAGCGTGGGGAGCAAACAGGATTAGATA

CCCTGGTAGTCCACGCCGTAAACGATGAATGTTAGCCGTCGGGCAGTTT

ACTGTTCGGTGGCGCAGCTAACGCATTAAACATTCCGCCTGGGGAGTAC

GGTCGCAAGATTAAAACTCAAAGGAATTGACGGGGGCCCGCACAAGCGG

TGGAGCATGTGGTTTAATTCGAAGCAACGCGCAGAACCTTACCAGCCCT

TGACATCCCGATCGCGGATTACGGAGACGTTTTCCTTCAGTTCGGCTGG

ATCGGAGACAGGTGCTGCATGGCTGTCGTCAGCTCGTGTCGTGAGATGT

TGGGTTAAGTCCCGCAACGAGCGCAACCCTCGCCCTTAGTTGCCAGCAT

TTAGTTGGGCACTCTAAGGGGACTGCCGGTGATAAGCCGAGAGGAAGGT

GGGGATGACGTCAAGTCCTCATGGCCCTTACGGGCTGGGCTACACACGT

GCTACAATGGTGGTGACAGTGGGCAGCGAGACCGCGAGGTCGAGCTAAT

CTCCAAAAGCCATCTCAGTTCGGATTGCACTCTGCAACTCGAGTGCATG

AAGTTGGAATCGCTAGTAATCGCAGATCAGCATGCTGCGGTGAATACGT

TCCCGGGCCTTGTACACACCGCCCGTCACACCATGGGAGTTGGTTCTAC

CCGAAGGTAGTGCGCTA -> 3'

Figure 3:
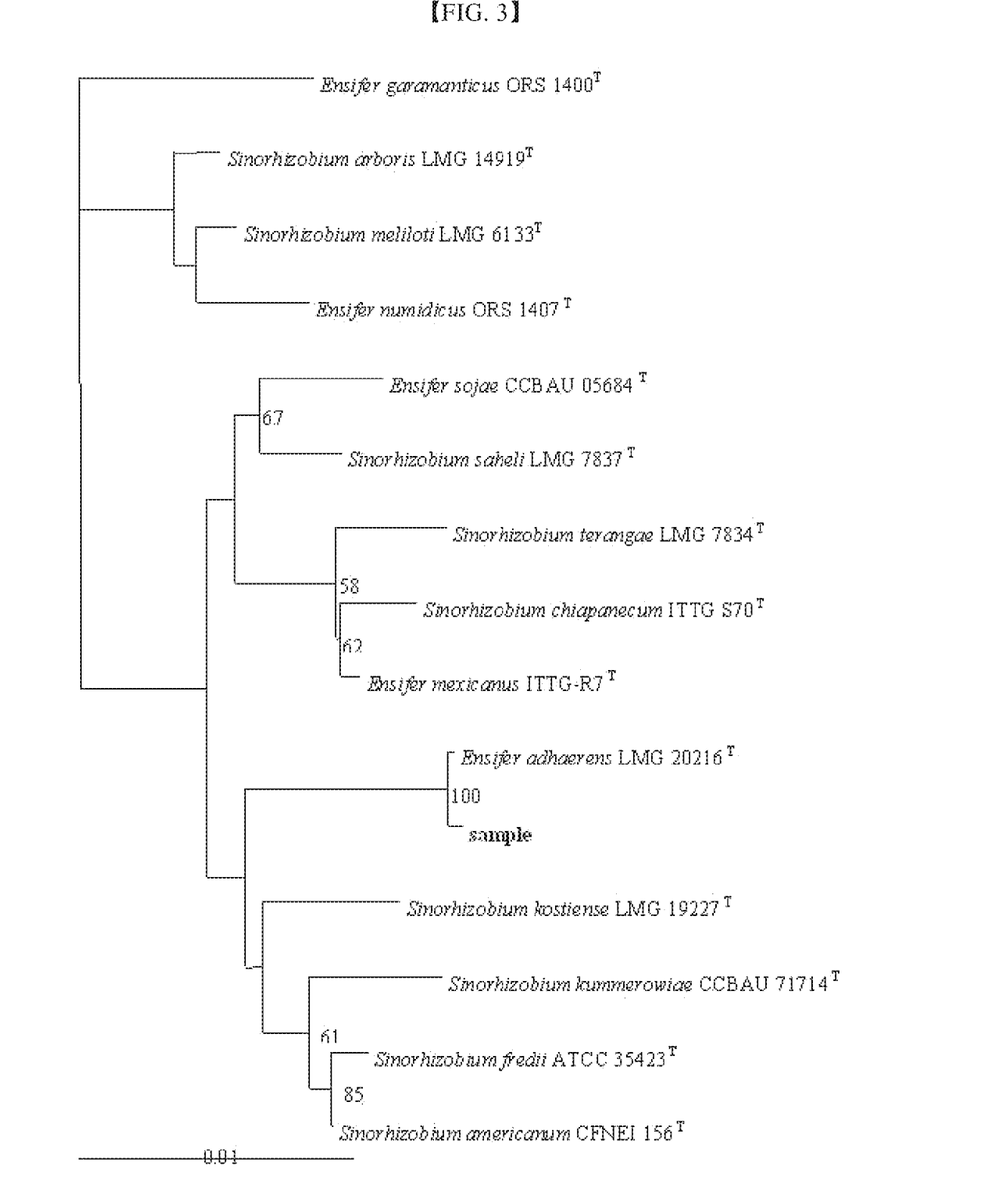
FIG. 3 is a result of phylogenetic tree analysis of isolated *Ensifer* sp. strain in accordance with an embodiment of present invention.

As shown in FIG. 3, the isolated strain showed 100% sequence identity of *Ensifer adhanerens* as a result of the phylogenetic tree of the isolated strain, and was designated as *Ensifer adhanerens* SYG29. The strain was deposited with Korean Culture Center of Microorganism (361-221, Yurim B/D Hongje-1-dong, Seodaemun-gu, SEOUL 120-091, Republic of Korea) on Mar. 29, 2013 under the Budapest Treaty, and then was received as an accession number of KCCM11405P.

The biochemical properties of the isolated strain were summarized in the following table.

TABLE 1

| Classification | reaction |
| --- | --- |
| Nitrate reduction | + |
| L-tryptophan degradation | − |
| D-glucose fermentation | − |
| Arginine dihydrolase | − |
| Urease | + |
| β-glucosidase | + |
| gelatin hydrolysis | − |
| β-galactosidase | + |
| D-glucose utilization | + |
| L-arabinose utilization | + |
| D-mannose utilization | + |
| D-mannitol utilization | + |
| N-acetyl glucosamine utilization | + |
| D-maltose utilization | + |
| Potassium gluconate utilization | − |
| Capric acid utilization | − |
| Adipic acid utilization | − |
| Malic acid utilization | + |
| Trisodium citrate utilization | − |
| Phenylacetic acid utilization | − |

Example 3: Determination of Optimal Production Condition of Psicose by Using the Cell Reaction In order to assay the psicose conversion rate on the changes in pH and temperature, the isolated strain was reacted with the substrate on various pH and temperature conditions, so as to compare the conversion rate of psicose.

3-1. The Activity Analysis on the Cell Concentration

In order to examine the minimal cell concentration for producing psicose, the isolated strains in Example 1 were incubated for 2 hours at 60° C. at cell concentration of 5 to 50 g(dcw)/L on 50 mM PIPES buffer (pH 7.0) added with 500 g/L fructose and 1 mM Mn ion. The reaction was stopped with centrifuging at 13,000 rpm, and the supernatant was heated for 5 minutes. Then, the reaction product was analyzed with HPLC analysis to measure the produced psicose. The HPLC analysis was performed by Refractive Index Detector (Agilent 1260 RID) equipped with Aminex HPX-87C column (BIO-RAD) at the condition as described above (solvent: water, temperature: 80° C., flow rate: 0.6 ml/min).

Figure 4:
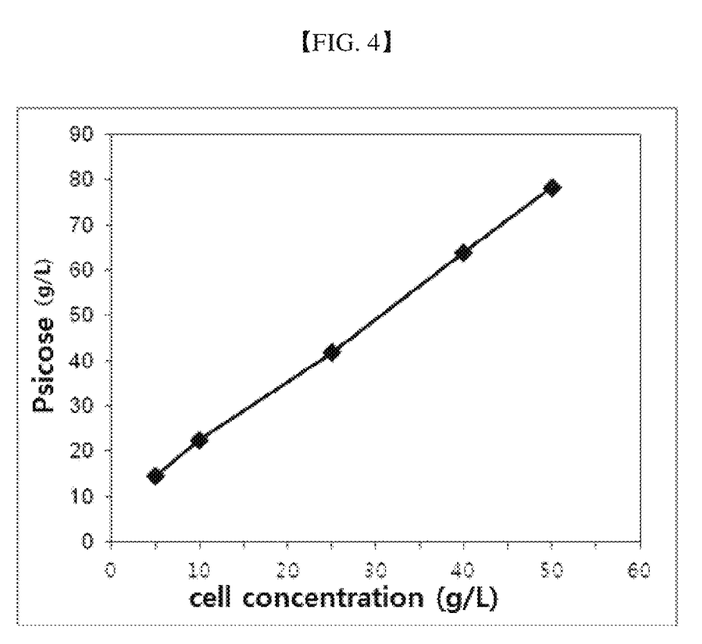
FIG. 4 is a graph showing the psicose productivity on the cell concentration.
Figure 5:
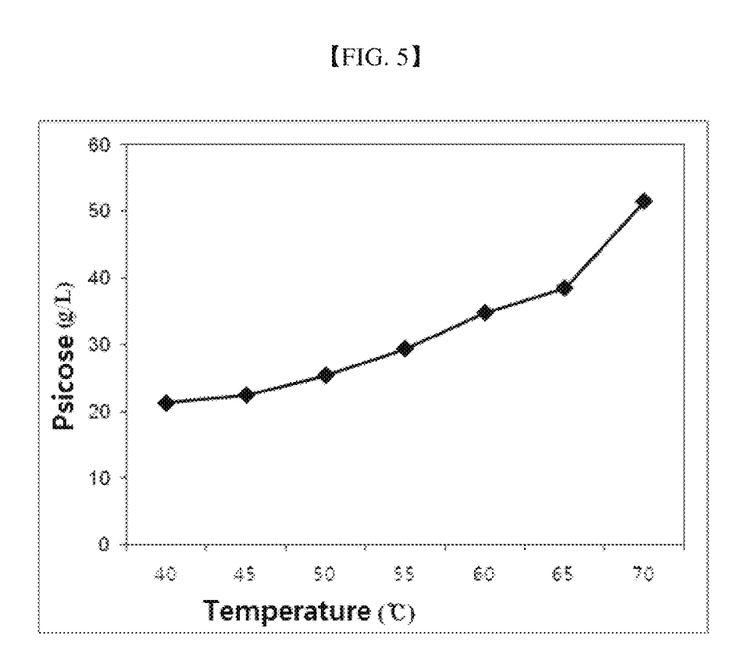
FIG. 5 is a graph showing the psicose productivity on the reaction temperature.

The result was shown in FIG. 4. As shown in FIG. 4, as the cell concentration of strain increased, the amount of produced psicose increased. As a result of cell reaction, when the cell concentration was 50 g(dcw)/L, the amount of produced psicose was 78.2 g/L as maximal experimental value. When the cell concentration was 5 g(dcw)/L, the conversion activity of strain was detected.

3-2. The Activity Analysis on the Reaction Temperature

To examine the optimal temperature on the psicose production, the cell reaction was performed under the same condition of Example 3-1 was performed, except that the strain isolated in Example 1 was reacted with the substrate at a cell concentration of 20 mg (dcw)/ml under the temperature of 40 to 70° C. After 2 hours reaction, the reaction was stopped and then analyzed with HPLC analysis to measure the amount of produced psicose according to the same method of Example 3-1.

3-3. The Activity Analysis on the Reaction pH

To examine the optimal pH condition on the psicose production, the cell reaction was performed under the same condition of Example 3-1 was performed, except that the strain isolated in Example 1 was reacted with the substrate at a cell concentration of 25 mg (dcw)/ml on McIlvaine (buffer solutions with various amounts of 0.1M citric acid and 0.2M disodium hydrogen phosphate solution to adjust pH condition) of pH 6.0-8.0 and 100 mM glycine pH 8.5 to 9.5 which were added with 500 g/L fructose and 1 mM Mn ion at 70° C. After the completion of reaction, the reaction was stopped and then analyzed with HPLC analysis to measure the amount of produced psicose according to the same method of Example 3-1.

Figure 6:
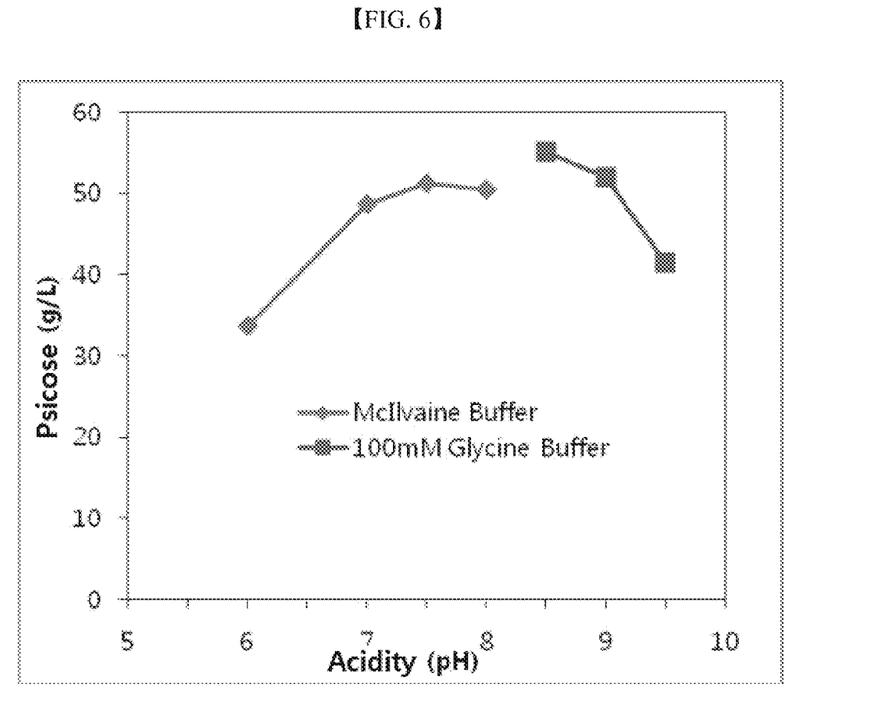
FIG. 6 is a graph showing the psicose productivity on the reaction pH.

The test result is shown in FIG. 6. As shown in FIG. 6, the conversion activity was high on pH 7.0-9.0. In the neutral pH condition of pH 7.0 to 8.0, the psicose could be produced efficiently.

3-4. The Activity Analysis on the Metal Ion

To examine the dependency of metal ions, the isolated strain was reacted with 50 mM PIPES (piperazine-N,N'-bis(2-ethanesulfonic acid)) buffer (pH 7.0) added by 400 g/L fructose at 55° C. in the presence of 1 mM metal ion of $CuCl_2$, $MnCl_2$, $CaCl_2$, $ZnSO_4$, $MgSO_4$, $NiSO_4$, $CoCl_2$, or $FeSO_4$ dissolved in PIPES. After the completion of reaction, the reaction was stopped and then analyzed with HPLC analysis to measure the amount of produced psicose according to the same method of Example 3-1.

Figure 7:
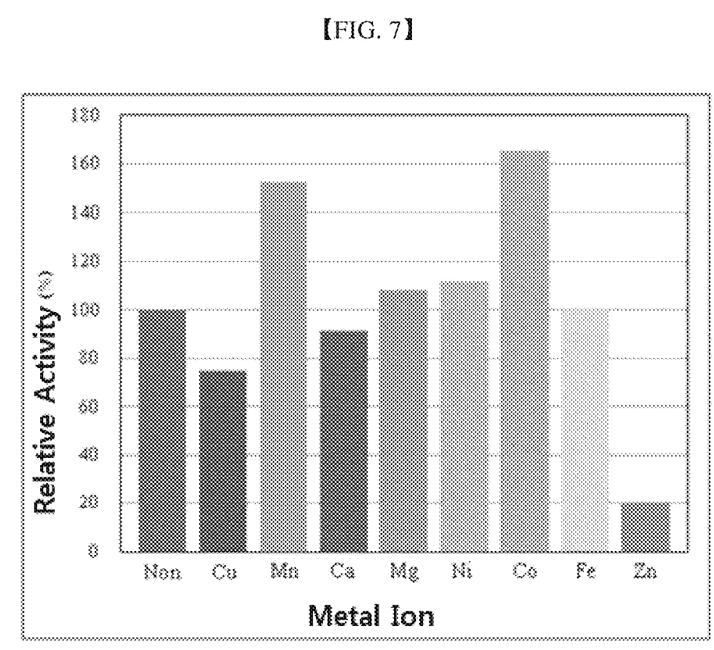
FIG. 7 is a graph showing the psicose productivity on the kinds of metal ions.

The test result is shown in FIG. 7. As shown in FIG. 7, the conversion activity was relatively high, when Mn ion and Co ion were used, by being compared to the absence of metal ion.

Example 4: Condition for Mass Production of Psicose 4-1. Psicose Productivity on Octylphenol Ethoxylate (TRITON X-100®; $C_{14}H_{22}O(C_2H_4O)n$; n=9 or 10) Concentration The addition of octylphenol ethoxylate (TRITON X-100®; n; n=9 or 10) concentration to increase the permeability of cell membrane can make the enzyme inside the cell membrane release, thereby shortening the production time of psicose.

In order to efficient production of psicose by using the cell reaction, the psicose productivity was analyzed by changing the added amount of octylphenol ethoxylate (TRITON X-100®; $C_{14}H_{22}O(C_2H_4O)n$; n=9 or 10). The reaction was performed at 60° C. for 2 hours and analyzed with HPLC according to the same method of Example 3-1 (fructose 500 g/L, 1 mM of Mn ion), except that the isolated strain was used at a cell concentration of 20 mg(dcw)/ml, with addition of 0 to 0.5% (v/v) of Triton X octylphenol ethoxylate (TRITON X-100®; $C_{14}H_{22}O(C_2H_4O)n$; n=9 or 10). After reaction completion, the amount of produced psicose was measured by HPLC analysis.

Figure 8:
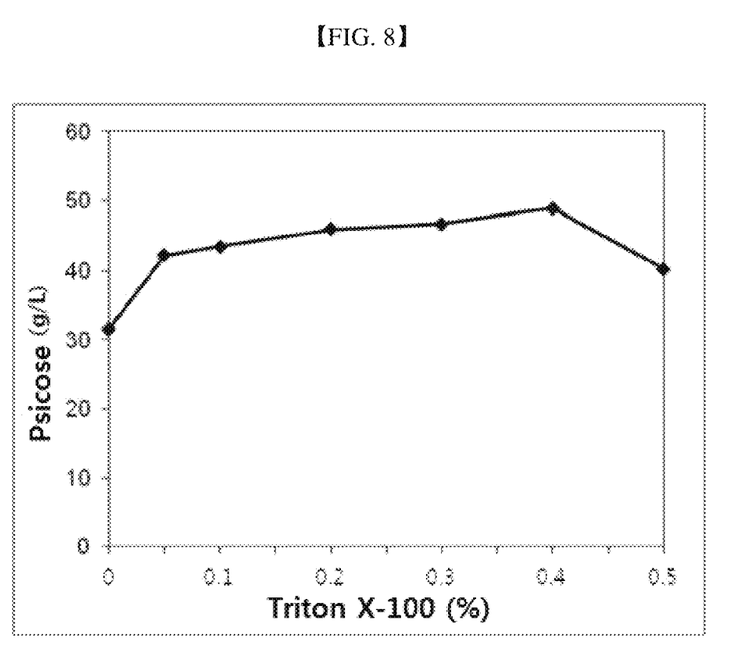
FIG. 8 is a graph showing the psicose productivity on the concentration of octylphenol ethoxylate (TRITON X-100®; $C_{14}H_{22}O(C_2H_4O)n$; n=9 or 10).

The HPLC analysis result was shown in FIG. 8. As indicated in FIG. 8, the reaction added by octylphenol ethoxylate (TRITON X-100®; $C_{14}H_{22}O(C_2H_4O)n$; n=9 or 10 showed the increased psicose production, compared to no addition of octylphenol ethoxylate (TRITON X-100®); $C_{14}H_{22}O(C_2H_4O)n$; n=9 or 10) (concentration of Triton X-100: 0% (v/v)). When the concentration of octylphenol ethoxylate (TRITON X-100®; $C_{14}H_{22}O(C_2H_4O)n$; n=9 or 10 was 0.4% (v/v), the highest psicose productivity was 48.9 g/L.

4-2. Thermal Stability of Cell

In order to examine the thermal stability of isolated strain, the strain obtained in Example 1 was suspended in 50 mM PIPES buffer solution added by 1 mM Mn ion and treated with thermal shock with heating at 55° C. or 60° C. for 22 hours. Then, the reaction was performed at 400 g/L of the final fructose concentration and 20 mg(dcw)/ml of cell concentration at 55° C. for additional 1 hour according to the same method of Example 3-1. The psicose productivity on heat shock time was measured by HPLC analysis.

Figure 9:
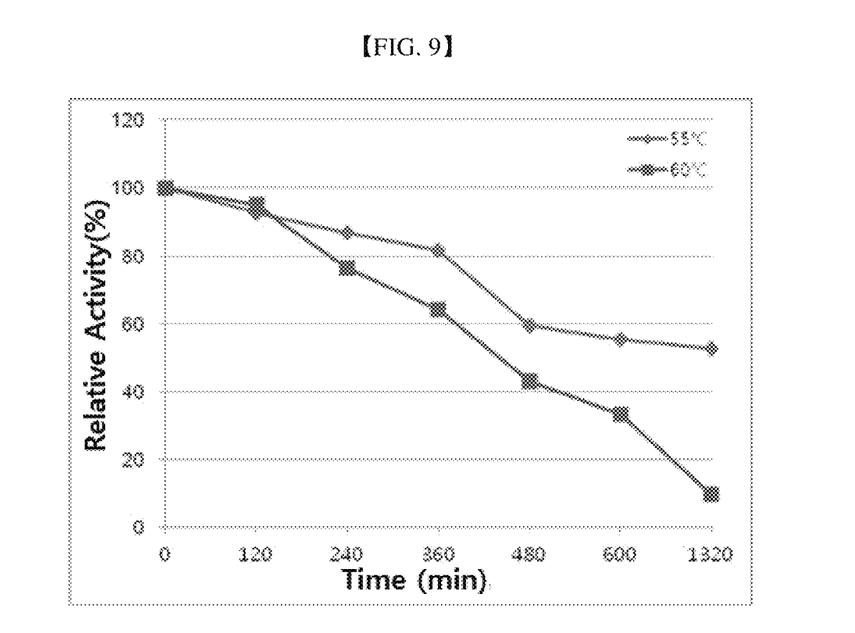
FIG. 9 is a graph showing the thermal stability of isolated *Ensifer* sp. strain on the temperature.

The HPLC analysis result was shown in FIG. 9. As indicated in FIG. 9, when the heat shock on the cell was given at 55° C., about 52% of the relative activity was maintained after 22 hours of heat shock, compare to no heat shock. when the heat shock on the cell was given at 60° C., the relative activity was decreased to about 10%. As a result, the half-life of cell activity was 456 minutes (7.6 hours).

4-3. Psicose Productivity

The maximal psicose productivity was tested under the established condition for mass production of psicose, by changing the reaction time. The strain isolated in Example 1 was reacted at 40 mg-dcw/ml of cell concentration, 500 g/L of fructose concentration and pH 7.0, at the temperatures of 40, 50, or 70° C. according to the method of Example 3-1. The reaction time was 6 hours, and the psicose productivity was analyzed with HPLC at 1 hour interval. The reaction was stop by heating at 100° C. for 5 minutes.

Figure 10:
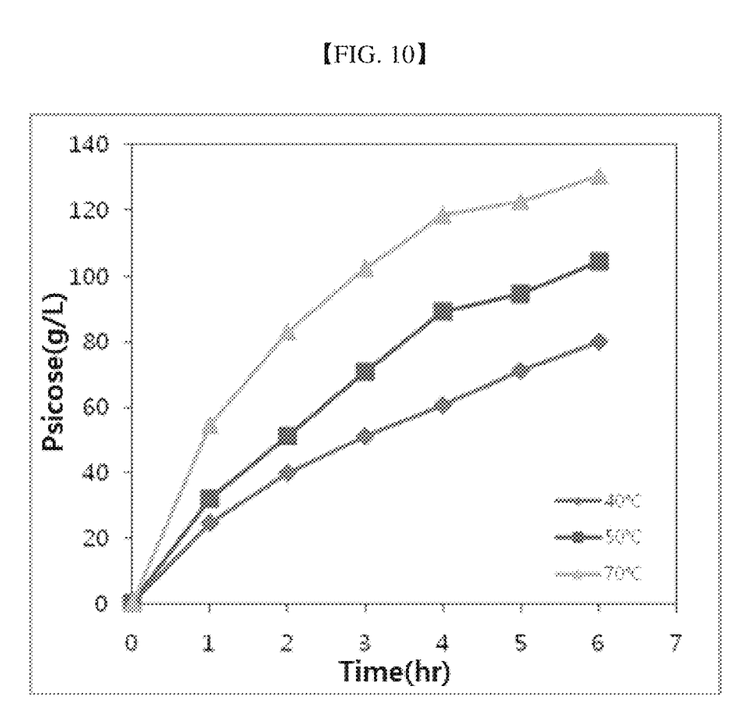
FIG. 10 is a graph showing the psicose productivity performed for 6 hours on various the reaction temperatures.

The HPLC analysis was shown in FIG. 10. As shown in FIG. 10, as the reaction temperature increased and the reaction time passed, the psicose productivity increased. Particularly, when the reaction was performed at 70° C. after 6 hour, the maximal psicose productivity was reached to be 130.3 g/L of amount of produced psicose, which was about 26% of conversion rate.

4-4. Psicose Productivity on Initial pH Condition

In order to test the possibility of mass production of psicose at initial pH condition, the substrate was dissolved in distilled water instead of buffer solution, and initial pH was adjusted with HCl and NaOH. By referring to the method of Example 3-1, the reaction was performed at 70° C. for 7 hours at fructose 400 g/L, 1 mM of Mn ion, at a cell concentration of 40 mg(dcw)/ml, with addition of 0.4% (v/v) of octylphenol ethoxylate (TRITON X-100®; $C_{14}H_{22}O(C_2H_4O)n$; n=9 or 10), on the initial pH conditions of 6.0, 6.5, or 7.0. After reaction completion, the amount of produced psicose was measured by HPLC analysis.

The HPLC analysis result was shown in FIG. 11. As indicated in FIG. 11, when the reaction was performed by using the substrate solution at initial pH of 7.0, the amount of produced psicose after 6 hour reaction was 97.3 g/L in the absence of buffer solution, to be 24.3% of conversion rate.

[Accession No.]

Depository Authority: Korean Culture Center of Microorganisms (361-221, Yurim B/D Hongje-1-dong, Seodaemun-gu, SEOUL 120-091, Republic of Korea)

Accession No.: KCCM11405P

Deposition Date: 29 Mar. 2013

---

The invention claimed is:

1. A method of producing psicose from fructose by using an *Ensifer* sp. strain, comprising:
   reacting an *Ensifer* sp. strain with fructose,
   wherein reacting the *Ensifer* sp. strain with fructose is performed by culturing the *Ensifer* sp. strain on culture medium containing fructose;
   mixing the fructose with at least one selected from the group consisting of: an *Ensifer* sp. strain cell, an *Ensifer* sp. strain cell culture, and an *Ensifer* sp. strain cell lysate; or
   contacting the fructose with a support immobilized with at least one selected from the group consisting of an *Ensifer* sp. strain cell, an *Ensifer* sp. strain cell culture, and an *Ensifer* sp. strain cell lysate, and wherein the *Ensifer* sp. strain is *Ensifer adhaerens*.

2. The method of claim 1, wherein the method further comprises a step of adding at least one metal ion selected from the group consisting of Cu, Mn, Ca, Mg, Zn, Ni, Co, Fe and Al ions.

3. The method of claim 1, wherein the method is performed without using a buffer solution.

4. The method of claim 1, wherein the method is performed at pH of 6 to 9 and at a temperature of 40 to 80° C.

5. A composition for producing psicose from fructose, comprising an *Ensifer* sp. strain,
   wherein the *Ensifer* sp. strain is *Ensifer adhaerens*, and
   wherein the *Ensifer adhaerens* is *Ensifer adhaerens* SYG29 deposited as accession number of KCCM11405P.

6. The composition of claim 5, wherein the *Ensifer* sp. strain is at least one selected from the group consisting of an *Ensifer* sp. strain cell, an *Ensifer* sp. strain cell culture, and an *Ensifer* sp. strain cell lysate.

7. A *Ensifer adhaerens* strain with an activity of converting fructose to psicose,
   wherein the *Ensifer adhaerens* is *Ensifer adhaerens* SYG29 deposited as accession number of KCCM11405P.

* * * * *